US008293518B2

(12) United States Patent
Igarashi et al.

(10) Patent No.: US 8,293,518 B2
(45) Date of Patent: Oct. 23, 2012

(54) MICROORGANISM AND METHOD FOR PRODUCING DODECAHYDRO-3A,6,6,9A-TETRAMETHYLNAPHTHO[2,1-B]FURAN INTERMEDIATE USING THE NOVEL MICROORGANISM

(75) Inventors: Kazuaki Igarashi, Tochigi (JP); Shuichi Takizawa, Tochigi (JP); Norihiko Higaki, Tochigi (JP); Hiroshi Hagihara, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/300,172

(22) Filed: Nov. 18, 2011

(65) Prior Publication Data

US 2012/0107917 A1  May 3, 2012

Related U.S. Application Data

(62) Division of application No. 12/280,067, filed as application No. PCT/JP2006/325516 on Dec. 21, 2006, now Pat. No. 8,084,237.

(30) Foreign Application Priority Data

Feb. 24, 2006  (JP) ................................. 2006-048550

(51) Int. Cl.
  C12N 1/16  (2006.01)
  C12N 1/14  (2006.01)
  C12P 17/04  (2006.01)
(52) U.S. Cl. .................... 435/254.1; 435/255.1; 435/126
(58) Field of Classification Search .......................... None
  See application file for complete search history.

(56) References Cited

U.S. PATENT DOCUMENTS

| 4,798,799 A | 1/1989 | Farbood et al. |
| 4,970,163 A | 11/1990 | Farbood et al. |
| 5,012,040 A | 4/1991 | Whitaker |
| 5,155,029 A | 10/1992 | Farbood et al. |
| 5,212,078 A | 5/1993 | Farbood et al. |
| 8,084,237 B2 | 12/2011 | Igarashi et al. |

FOREIGN PATENT DOCUMENTS

| EP | 0 204 009 A1 | 12/1986 |
| JP | 62-74281 A | 4/1987 |
| JP | 3-224478 A | 10/1991 |
| JP | 4-126023 A | 4/1992 |
| JP | 2547713 B2 | 10/1996 |
| JP | 2802588 B2 | 9/1998 |
| JP | 3002654 B2 | 1/2000 |

OTHER PUBLICATIONS

Aranda, G., et al., "Microbial Transformation of Diterpenes: Hydroxylation of Sclareol, Manool and Derivatives by *Mucor plumbeus*," Tetrahedron 47:8339-8350, Pergamon Press plc (1991).
Aranda, G., et al., "Microbial Hydroxylation of Sclareol by *Mucor plumbeus*," Tetrahedron Letts. 32: 1783-1786, Pergamon Press plc (1991).
Dialog File 351, Accession No. 3781232, English language abstract and patent family for JP 62-74281 A, published Apr. 6, 1987.
Dialog File 351, Accession No. 3781232, English language abstract and patent family for JP 2547713 B2, issued Oct. 23, 1996.
Dialog File 351, Accession No. 5361451, English language abstract and patent family for JP 2802588 B2, issued Sep. 24, 1998, and for JP 3002654 B2, issued Jan. 24, 2000.
Patent Abstract of Japan, English language abstract of JP 03-22448 A published, Oct. 3, 1991.
Patent Abstract of Japan, English language abstract of JP 04-126023 A published, Apr. 27, 1992.
Extended European Search Report for corresponding EPO Application No. 06835082.6-2406, mailed Jul. 21, 2009, European Patent Office, Munich, Germany.
International Preliminary Report on Patentability for International Application No. PCT/JP2006/325516, (English translation), Internationl Bureau of WIPO, Geneva, Switzerland, issued on Aug. 26, 2008.
International Search Report for International Application No. PCT/JP2006/325516, Japanese Patent Office, mailed on Jan. 23, 2007.
Written Opinion of the International Searching Authority for International Application No. PCT/JP2006/325516, (English translation), International Bureau of WIPO, Geneva, Switzerland, mailed Jan. 23, 2007.
Wikipedia, "Ascomycota," Wikipedia.org, accessed at http://en.wikipedia.org/wiki/Ascomycota, 13 pages, 2011.

*Primary Examiner* — Tekchand Saidha
*Assistant Examiner* — Md. Younus Meah
(74) *Attorney, Agent, or Firm* — Sterne, Kessler, Goldstein & Fox P.L.L.C.

(57) ABSTRACT

This invention relates to a novel microorganism that efficiently produces a dodecahydro-3a,6,6,9a-tetramethylnaphtho[2,1-b]furan intermediate using sclareol as a substrate. As a result of concentrated studies, a plurality of novel microorganisms having properties of interest that are not classified as conventional microorganisms were isolated and identified. The novel microorganism of the present invention belongs to *Ascomycetes* and has the ability of producing a dodecahydro-3a,6,6,9a-tetramethylnaphtho[2,1-b]furan intermediate using sclareol as a substrate. Such microorganism of *Ascomycetes* represents a new finding and it can be effective for producing dodecahydro-3a,6,6,9a-tetramethylnaphtho[2,1-b]furan and an intermediate thereof.

6 Claims, 1 Drawing Sheet

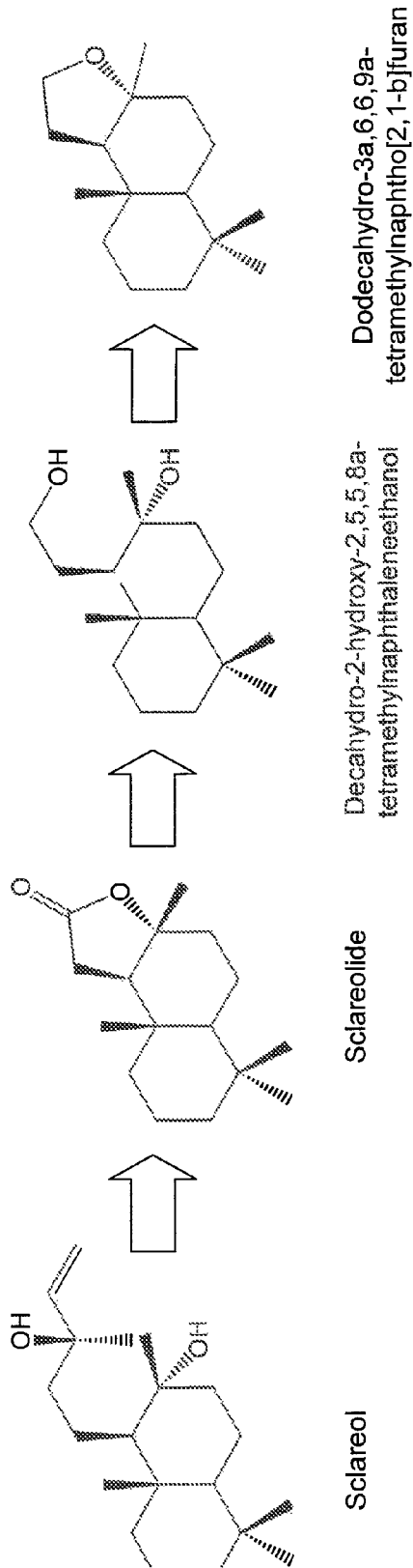

MICROORGANISM AND METHOD FOR PRODUCING DODECAHYDRO-3A,6,6,9A-TETRAMETHYLNAPHTHO[2,1-B]FURAN INTERMEDIATE USING THE NOVEL MICROORGANISM

CROSS-REFERENCE TO RELATED APPLICATIONS

This application is a divisional of U.S. patent application Ser. No. 12/280,067, §371 Date Aug. 20, 2008, now U.S. Pat. No. 8,084,237, which is the U.S. National Phase of International Application No. PCT/JP2006/325516, international filing date of Dec. 21, 2006, and which claims benefit of the filing date of Japanese Patent Application No. 2006-048550, filed Feb. 24, 2006, the disclosures of each of which is herein incorporated by reference in its entirety.

TECHNICAL FIELD

The present invention relates to a novel microorganism that produces a dodecahydro-3a,6,6,9a-tetramethylnaphtho[2,1-b]furan intermediate using sclareol as a substrate. Further, the present invention relates to a method for producing a dodecahydro-3a,6,6,9a-tetramethylnaphtho[2,1-b]furan intermediate using the novel microorganism.

BACKGROUND ART

Dodecahydro-3a,6,6,9a-tetramethylnaphtho[2,1-b]furan (occasionally referred to as "Ambroxan (trademark)") is an aroma chemical with satisfactorily long-lasting properties that is produced via chemical conversion mainly from sclareol extracted from *Salvia sclarea*. FIG. 1 shows a process for producing dodecahydro-3a,6,6,9a-tetramethylnaphtho[2,1-b]furan from sclareol. As shown in FIG. 1, decahydro-2-hydroxy-2,5,5,8a-tetramethylnaphthaleneethanol and sclareolide (decahydro-3a,6,6,9a-tetramethylnaphtho[2,1-b]furan-2(1H)-one) are known as dodecahydro-3a,6,6,9a-tetramethylnaphtho[2,1-b]furan intermediates. Also, a cyclic ether compound (8α,13-oxido-12,13-dehydro-15,16-dinorlabdane) is known as a dodecahydro-3a,6,6,9a-tetramethylnaphtho[2,1-b]furan intermediate, although it is not shown in FIG. 1.

Conversion of sclareol into a dodecahydro-3a,6,6,9a-tetramethylnaphtho[2,1-b]furan intermediate by a microorganism is described in, for example, JP Patent No. 2547713, JP Patent No. 2802588, JP Patent No. 3002654, and JP Patent No. 2063550. JP Patent No. 2547713 discloses production of decahydro-2-hydroxy-2,5,5,8a-tetramethylnaphthaleneethanol by *Hyphozyma roseoniger* ATCC20624. JP Patent No. 2802588 discloses production of a dodecahydro-3a,6,6,9a-tetramethylnaphtho[2,1-b]furan intermediate by *Cryptococcus laurentii* ATCC20920. JP Patent No. 3002654 discloses production of a dodecahydro-3a,6,6,9a-tetramethylnaphtho[2,1-b]furan intermediate by *Bensingtonia cilliata* ATCC20919. JP Patent No. 2063550 discloses production of a dodecahydro-3a,6,6,9a-tetramethylnaphtho[2,1-b]furan intermediate by *Cryptococcus albidus* ATCC20918 and *Cryptococcus albidus* ATCC20921.

Thus, only microorganisms of *Basidiomycetes* or *Hyphozyma* were known as microorganisms having the ability of producing dodecahydro-3a,6,6,9a-tetramethylnaphtho[2,1-b]furan intermediates using sclareol as a substrate, as disclosed in JP Patent No. 2547713, JP Patent No. 2802588, JP Patent No. 3002654, and JP Patent No. 2063550.

DISCLOSURE OF THE INVENTION

Problems to be Solved by the Invention

Under the above circumstances, the present invention is intended to provide a novel microorganism that can efficiently produce a dodecahydro-3a,6,6,9a-tetramethylnaphtho[2,1-b]furan intermediate using sclareol as a substrate. Further, the present invention is intended to provide a method for producing a dodecahydro-3a,6,6,9a-tetramethylnaphtho[2,1-b]furan intermediate using such microorganism.

Means for Solving the Problems

In order to solve the above problems, the present inventors have conducted concentrated studies on soil samples as the sources of microorganisms obtained from Haga Gun, Tochigi, Japan, and Utsunomiya City, Tochigi, Japan, for the purpose of isolating and identifying microorganisms having properties of interest. As a result, they succeeded in isolating and identifying three strains of novel microorganisms that are not classified as conventional microorganisms and that have properties of interest. The present invention has been completed based on findings to the effect that a dodecahydro-3a,6,6,9a-tetramethylnaphtho[2,1-b]furan intermediate can be produced using sclareol as a substrate, the same being possessed by the above novel microorganisms.

The novel microorganisms according to the present invention belong to *Ascomycetes* and have the ability of producing a dodecahydro-3a,6,6,9a-tetramethylnaphtho[2,1-b]furan intermediate using sclareol as a substrate. Microorganisms of *Ascomycetes* having such ability represent novel findings, and such microorganisms can be useful for producing dodecahydro-3a,6,6,9a-tetramethylnaphtho[2,1-b]furan and an intermediate thereof. Regarding novel microorganisms that had been isolated and identified by the present inventors, the nucleotide sequences of the genes encoding 28S rRNA (hereafter referred to as "28S rDNA") were identified. Such nucleotide sequences are as shown in SEQ ID NOs: 1 to 3. Regarding the novel microorganisms, the nucleotide sequences of the genes encoding 18S rRNA (hereafter referred to as "18S rDNA") were identified. Such nucleotide sequences are as shown in SEQ ID NOs: 4 to 6. Further, the novel microorganisms were found to have mycological properties shown in Table 1.

TABLE 1

|  | KSM-JL2842 | KSM-J3571 | KSM-JL4651 |
|---|---|---|---|
| Carbon source assimilability test |  |  |  |
| D-Glucose | + | + | + |
| D-Galactose | + | + | + |
| L-Sorbose | + | + | w |
| D-Ribose | w | w | w |
| D-Xylose | + | + | + |
| L-Arabinose | + | + | + |
| D-Arabinose | + | w | w |
| L-Rhamnose | + | + | + |
| Sucrose | + | + | + |
| Maltose | + | + | + |
| α,α-Trehalose | + | + | + |
| Me α-D-glucoside | + | + | w |
| D-Cellobiose | + | + | + |
| Salicin | − | w | w |
| Melibiose | + | + | + |
| Lactose | + | + | w |
| D-Raffinose | + | + | + |

TABLE 1-continued

|  | KSM-JL2842 | KSM-J3571 | KSM-JL4651 |
|---|---|---|---|
| Melezitose | + | + | + |
| Inulin | − | w | − |
| Soluble starch | w | + | + |
| Glycerol | + | + | w |
| meso-Erythritol | + | + | w |
| Ribitol | w | − | w |
| D-Sorbitol | + | + | w |
| D-Mannitol | + | + | w |
| D-Galactitol | − | − | − |
| myo-Inositol | + | w | w |
| Glucono-1,5-lactone | w | w | − |
| Ca 2-keto-gluconic acid | − | − | w |
| Ca 5-keto-gluconic acid | − | − | w |
| DL-Lactate | + | + | w |
| Succinate | + | + | + |
| Citrate | − | w | w |
| Methanol | − | − | − |
| Sugar fermentability test | | | |
| D-Glucose | − | − | − |
| Nitrogen source assimilability test | | | |
| Potassium nitrate | + | + | + |

The present inventors attempted to identify novel microorganisms based on the nucleotide sequences of 28S rDNA as shown in SEQ ID NOs: 1 to 3, the nucleotide sequences of 18S rDNA as shown in SEQ ID NOs: 4 to 6, and mycological properties shown in Table 1. As a result, they were able to discern only that the novel microorganisms belonged to *Ascomycetes*. Specifically, the novel microorganisms were not classified into known genera or species of *Ascomycetes*. Thus, such novel microorganisms were concluded to belong to a novel genus. Classification in terms of mycological properties was performed in accordance with Barnett, J. A., Payne, R. W., and Yarrow, D., 2000, Yeasts: Characteristics and identification, 3$^{rd}$ edition, Cambridge University Press, Cambridge, U.K.; and Kurtzman, C. P. and Fell, J. W., 1998, The Yeasts, a taxonomic study, 4$^{th}$ edition, Elsevier, Amsterdam, Netherlands.

The novel microorganisms were deposited at the International Patent Organism Depositary of the National Institute of Advanced Industrial Science and Technology (IPOD: Tsukuba Central 6, 1-1-1 Higashi, Tsukuba, Ibaraki, 305-8566, Japan) as of Jan. 12, 2006, under the accession numbers FERM BP-10713 and FERM BP-10712 and as of Jul. 13, 2006, under the accession number FERM BP-10714.

Specifically, the microorganisms of the present invention belong to *Ascomycetes* and have the ability of producing an intermediate during the process of synthesizing dodecahydro-3a,6,6,9a-tetramethylnaphtho[2,1-b]furan using sclareol as a substrate. Also, it is preferable that the microorganisms of the present invention comprise 28S rDNA consisting of a nucleotide sequence having 95% or higher identity to the nucleotide sequence as shown in any of SEQ ID NOs: 1 to 3 or 18S rDNA consisting of a nucleotide sequence having 95% or higher identity to the nucleotide sequence as shown in any of SEQ ID NOs: 4 to 6. Further, the microorganisms of the present invention preferably have the mycological properties shown in Table 1. Furthermore, the microorganisms of the present invention are preferably of ascomycetous yeast strains that are identified by the accession number FERM BP-10713, FERM BP-10712, or FERM BP-10714. The microorganisms of the present invention may belong to the genus, preferably the species, and more preferably the strain to which the ascomycetous yeast strains belong.

Examples of the intermediates of the present invention include decahydro-2-hydroxy-2,5,5,8a-tetramethylnaphthaleneethanol and/or sclareolide (decahydro-3a,6,6,9a-tetramethylnaphtho[2,1-b]furan-2(1H)-one).

The present invention can provide a method for producing a dodecahydro-3a,6,6,9a-tetramethylnaphtho[2,1-b]furan intermediate using the novel microorganisms of the present invention. Specifically, the method for producing a dodecahydro-3a,6,6,9a-tetramethylnaphtho[2,1-b]furan intermediate according to the present invention comprises culturing the novel microorganisms in a sclareol-containing medium and producing an intermediate during the process of synthesizing dodecahydro-3a,6,6,9a-tetramethylnaphtho[2,1-b]furan using sclareol as a substrate.

Effects of the Invention

The present invention can provide novel microorganisms that belong to *Ascomycetes* and that have the ability of producing an intermediate during the process of synthesizing dodecahydro-3a,6,6,9a-tetramethylnaphtho[2,1-b]furan using sclareol as a substrate. Dodecahydro-3a,6,6,9a-tetramethylnaphtho[2,1-b]furan, which is a starting material for an aroma chemical or the like, can be produced from such intermediate. Accordingly, use of the novel microorganisms of the present invention enables production of dodecahydro-3a,6,6,9a-tetramethylnaphtho[2,1-b]furan at low cost.

The present invention can also provide a method for producing a dodecahydro-3a,6,6,9a-tetramethylnaphtho[2,1-b]furan intermediate, which is a starting material for dodecahydro-3a,6,6,9a-tetramethylnaphtho[2,1-b]furan as a starting material for an aroma chemical or the like. According to the method for producing a dodecahydro-3a,6,6,9a-tetramethylnaphtho[2,1-b]furan intermediate of the present invention, dodecahydro-3a,6,6,9a-tetramethylnaphtho[2,1-b]furan can be produced at low cost.

This description includes part or all of the contents as disclosed in the description and/or drawings of Japanese Patent Application No. 2006-048550, which is a priority document of the present application.

BRIEF DESCRIPTION OF THE DRAWINGS

FIG. 1 shows a process for producing dodecahydro-3a,6,6,9a-tetramethylnaphtho[2,1-b]furan from sclareol.

BEST MODES FOR CARRYING OUT THE INVENTION

Hereafter, the present invention is described in detail.
Novel Microorganisms

The novel microorganisms of the present invention belong to *Ascomycetes* and produce an intermediate, i.e., a dodecahydro-3a,6,6,9a-tetramethylnaphtho[2,1-b]furan intermediate, during the process of synthesizing dodecahydro-3a,6,6,9a-tetramethylnaphtho[2,1-b]furan using sclareol as a substrate. The term "dodecahydro-3a,6,6,9a-tetramethylnaphtho[2,1-b]furan intermediate" used herein refers to decahydro-2-hydroxy-2,5,5,8a-tetramethylnaphthaleneethanol and sclareolide (decahydro-3a,6,6,9a-tetramethylnaphtho[2,1-b]furan-2(1H)-one).

The novel microorganisms of the present invention can be isolated from soil using the ability of producing a dodecahydro-3a,6,6,9a-tetramethylnaphtho[2,1-b]furan intermediate as an indicator. The ability of producing a dodecahydro-3a,6,6,9a-tetramethylnaphtho[2,1-b]furan intermediate can be evaluated by culturing test microorganisms in a sclareol-containing medium and detecting a dodecahydro-3a,6,6,9a-tetramethylnaphtho[2,1-b]furan intermediate in the medium. A dodecahydro-3a,6,6,9a-tetramethylnaphtho[2,1-b]furan intermediate in the medium can be detected by extracting the dodecahydro-3a,6,6,9a-tetramethylnaphtho[2,1-b]furan intermediate, using an organic solvent, from the medium from which the test microorganisms have been removed, and then performing, for example, gas chromatography (GC).

Methods for detecting the dodecahydro-3a,6,6,9a-tetramethylnaphtho[2,1-b]furan intermediate are not limited to GC. For example, conventional methods of analysis, such as gas-liquid chromatography (GLC), thin-layer chromatography (TLC), high pressure liquid chromatography (HPLC), infrared spectrum (IR), or nuclear magnetic resonance (NMR), can be employed.

The present inventors have isolated the novel microorganisms of *Ascomycetes* from soil samples of Haga Gun, Tochigi, Japan, and Utsunomiya City, Tochigi, Japan, via such means. The isolated, novel microorganisms are cultured in a sclareol-containing medium, so that such microorganisms can produce dodecahydro-3a,6,6,9a-tetramethylnaphtho[2,1-b]furan intermediates in the medium. The present inventors designated these novel microorganisms as *Ascomycete* sp. KSM-JL2842, *Ascomycete* sp. KSM-J3571, and *Ascomycete* sp. KSM-JL4651 and deposited them at the International Patent Organism Depositary of the National Institute of Advanced Industrial Science and Technology (IPOD: Tsukuba Central 6, 1-1-1 Higashi, Tsukuba, Ibaraki, 305-8566, Japan) under the accession numbers FERM BP-10713, FERM BP-10712, and FERM BP-10714.

The novel microorganisms of the present invention include microorganisms that belong yeast strains of *Ascomycetes* identified by the accession number FERM BP-10713, FERM BP-10712, or FERM BP-10714, microorganisms that are classified into the same genus as that of the yeast strains, preferably, into the same species, and more preferably, into the same strain as the yeast strains. Also, such microorganisms have the ability of producing dodecahydro-3a,6,6,9a-tetramethylnaphtho[2,1-b]furan intermediates.

The ascomycetous yeast strains identified by the accession numbers FERM BP-10713, FERM BP-10712, and FERM BP-10714 have 28S rDNA comprising the nucleotide sequences as shown in any of SEQ ID NOs: 1, 2, and 3, respectively. Accordingly, the novel microorganisms of the present invention include ascomycetous yeast strains having 28S rDNA comprising a nucleotide sequence having 95% or higher, preferably 98% or higher, and more preferably 99% or higher identity to any one of the nucleotide sequences as shown in any of SEQ ID NOs: 1 to 3 and having the ability of producing dodecahydro-3a,6,6,9a-tetramethylnaphtho[2,1-b]furan intermediates.

Further, ascomycetous yeast strains identified by the accession numbers FERM BP-10713, FERM BP-10712, and FERM BP-10714 have 18S rDNA comprising the nucleotide sequences as shown in SEQ ID NOs: 4, 5, and 6, respectively. Accordingly, the novel microorganisms of the present invention include ascomycetous yeast strains having 18S rDNA comprising a nucleotide sequence having 95% or higher, preferably 98% or higher, and more preferably 99% or higher identity to any one of the nucleotide sequences as shown in any of SEQ ID NOs: 4 to 6 and having the ability of producing dodecahydro-3a,6,6,9a-tetramethylnaphtho[2,1-b]furan intermediates.

Production of dodecahydro-3a,6,6,9a-tetramethylnaphtho[2,1-b]furan Intermediate by Novel Microorganisms With the use of the novel microorganisms of the present invention described above, dodecahydro-3a,6,6,9a-tetramethylnaphtho[2,1-b]furan intermediates can be produced. The produced dodecahydro-3a,6,6,9a-tetramethylnaphtho[2,1-b]furan intermediates can be used as starting materials for producing dodecahydro-3a,6,6,9a-tetramethylnaphtho[2,1-b]furan, which is a new aroma chemical of high value with satisfactorily long-lasting properties.

When producing dodecahydro-3a,6,6,9a-tetramethylnaphtho[2,1-b]furan intermediates with the use of the novel microorganisms of the present invention, the novel microorganisms of the present invention are first cultured in a sclareol-containing medium. A medium of any composition can be used, provided that microorganisms of *Ascomycetes* can grow therein. Examples of medium that can be used include solid medium and liquid medium containing carbon sources, nitrogen sources, minerals, and vitamins. A medium for culturing the novel microorganisms of the present invention may contain a surfactant or an antifoaming agent, in accordance with culture conditions or the like.

Examples of carbon sources to be added to the medium include monosaccharide, disaccharide, oligosaccharide, and polysaccharide. They may be used in combinations of two or more. Examples of carbon sources other than saccharides include organic acid salts, such as acetic acid salts. These carbon sources may be used independently or in combinations of two or more according to need.

Examples of nitrogen sources include inorganic and organic ammonium salts, such as ammonia, ammonium chloride, ammonium sulfate, ammonium nitrate, ammonium carbonate, ammonium phosphate, and ammonium acetate, nitrogen-containing organic substances, such as urea, peptone, meat extract, yeast extract, and casein hydrolysate, and amino acids, such as glycine, glutamic acid, alanine, and methionine. These nitrogen sources May be used independently or in combinations of two or more according to need.

Further, examples of minerals include sodium chloride, ferrous sulfate, magnesium sulfate, manganese sulfate, zinc sulfate, and calcium carbonate. Each mineral can be used independently or in combinations of two or more according to need.

Conditions for culturing the novel microorganisms of the present invention are not particularly limited, and culture can be carried out at the optimal pH level and temperature. Specifically, an optimal pH level is 3 to 8, preferably 4 to 8, and more preferably 5 to 7. Optimal temperature is 10° C. to 35° C., preferably 15° C. to 30° C., and more preferably 20° C. to 30° C. Culture can be conducted via, for example, shake culture, anaerobiotic culture, stationary culture, or culture in a fermenter. In addition, a resting cell reaction and an immobilized-cell reaction can also be employed.

A concentration of sclareol to be added to a medium having such composition is not particularly limited, and such concentration is preferably 0.1% to 50%. Sclareol may be added to the medium prior to the culture or during the culture (i.e., feeding culture). Also, components other than sclareol, such as carbon sources, nitrogen sources, vitamins, minerals, surfactants, or antifoaming agents, can be simultaneously fed.

Dodecahydro-3a,6,6,9a-tetramethylnaphtho[2,1-b]furan intermediates can be recovered from a medium after culturing the novel microorganisms as described above. Dodecahydro-3a,6,6,9a-tetramethylnaphtho[2,1-b]furan intermediates can be recovered from a medium in accordance with a conventional technique, without particular limitation. For example, cells are separated and removed from a medium, and dodecahydro-3a,6,6,9a-tetramethylnaphtho[2,1-b]furan intermediates an be isolated and purified with the use of combinations of centrifugation, ultrafiltration, ion-exchange chromatography, reverse osmosis membrane filtration, electrodialysis, salting out, crystallization, and other means.

A method for producing dodecahydro-3a,6,6,9a-tetramethylnaphtho[2,1-b]furan using the resulting dodecahydro-3a,6,6,9a-tetramethylnaphtho[2,1-b]furan intermediates is not particularly limited, and an adequate conventional technique can be employed. Specifically, sclareolide is reduced with, for example, lithium aluminum hydride, sodium borohydride, or a potassium borohydride/lithium chloride mixture to give decahydro-2-hydroxy-2,5,5,8a-tetramethylnaphthaleneethanol. Decahydro-2-hydroxy-2,5,5,8a-tetramethylnaphthaleneethanol is subjected to cyclodehydration in various types of solvents with the use of acidic catalysts, such as p-toluenesulfonic acid, p-toluenesulfonic acid chloride, or catalytic amounts of sulfuric acid and acidic ion-exchanger to give dodecahydro-3a,6,6,9a-tetramethylnaphtho[2,1-b]furan.

EXAMPLES

Hereafter, the present invention is described in greater detail with reference to the examples, although the technical scope of the present invention is not limited to the following examples.

Example 1

Isolation of Novel Microorganisms

Novel microorganisms were isolated from soil samples of Haga Gun, Tochigi, Japan, and Utsunomiya City, Tochigi, Japan, in the following manner.

At the outset, 100 μl of a soil suspension was applied to an agar medium containing 0.2% yeast extract, 0.2% ammonium nitrate, 0.1% monopotassium phosphate, 0.05% magnesium sulfate heptahydrate, 2.0% agar, 1.0% sclareol (separately sterilized), and 0.5% Tween 80 (separately sterilized). Culture was conducted at 25° C. for 7 to 14 days, the grown colonies were inoculated into a liquid medium containing 0.2% yeast extract, 0.2% ammonium nitrate, 0.1% monopotassium phosphate, and 0.05% magnesium sulfate heptahydrate, and culture was conducted at 25° C. for 1 day to provide starter strains. Subsequently, the starter strains were inoculated into a medium containing 0.2% yeast extract, 0.2% ammonium nitrate, 0.1% monopotassium phosphate, 0.05% magnesium sulfate heptahydrate, 1.0% sclareol (separately sterilized), and 0.5% Tween 80 (separately sterilized) to a concentration of 1%, and culture was conducted at 25° C. for 1 week.

After the completion of culture, a target substance was extracted from 0.1 ml of a culture solution with 0.6 ml of ethyl acetate, adequately diluted, and then subjected to gas chromatography (GC) analysis. Analysis was carried out using the Agilent technologies 6890N as a GC analyzer under the following conditions. A Flame Ionization Detector (FID) was used as a detector, the inlet temperature was set at 250° C., a split injection mode was used with a split ratio of 100:1, the total flow rate was 200 ml/min, the column flow rate was 0.4 ml/min, the DB-WAX (φ 0.1 mm×10 m, J&W) column was used as a column, and the oven temperature was 250° C. Under such conditions, a cyclic ether compound, i.e., a dodecahydro-3a,6,6,9a-tetramethylnaphtho[2,1-b]furan intermediate, exhibited a peak at around 0.8 minutes, sclareolide exhibited a peak at around 2.4 minutes, sclareol exhibited a peak at around 2.7 minutes, and decahydro-2-hydroxy-2,5,5,8a-tetramethylnaphthaleneethanol exhibited a peak at around 3 minutes.

Under such conditions, 6,950 starter strains were evaluated in terms of the ability of producing dodecahydro-3a,6,6,9a-tetramethylnaphtho[2,1-b]furan intermediates. As a result, novel microorganisms having the ability of producing mainly decahydro-2-hydroxy-2,5,5,8a-tetramethylnaphthaleneethanol were isolated. The isolated novel microorganisms were designated as KSM-JL2842, KSM-J3571, and KSM-JL4651.

Example 2

Classification of Novel Microorganisms

Mycological properties of KSM-JL2842, KSM-J3571, and KSM-JL4651 isolated in Example 1 were identified and rDNAs thereof were analyzed in an attempt to classify such strains.

At the outset, mycological properties of KSM-JL2842 were identified in the following manner. A wet and pale red colony was observed on YM agar (Becton Dickinson) plate medium, and the shape of the peripheral portion of the colony was relatively smooth. Microscopic features thereof were observed. As a result, formation of egg-shaped to oval and cylindrical trophocytes was observed, and trophocytes were found to proliferate due to gemmation. As a result of a biochemical property test, the results shown in Table 2 were obtained. In Table 2, the symbol "+" indicates a positive result, the symbol "−" indicates a negative result, and the symbol "w" indicates a weak positive result. Also, KSM-JL2842 grew at 25° C. but did not grow at 30° C. or higher.

Mycological properties of KSM-J3571 were identified in the following manner. A wet and pale red to yellowish red colony was observed on YM agar (Becton Dickinson) plate medium, and the shape of the peripheral portion of the colony was smooth. Microscopic features thereof were observed. As a result, formation of egg-shaped to oval and spindle trophocytes was observed, and trophocytes were found to proliferate due to gemmation. As a result of a biochemical property test, the results shown in Table 2 were obtained. Also, KSM-J3571 grew at 25° C., grew weakly at 30° C., but did not grow at 35° C. or higher.

Mycological properties of KSM-JL4651 were identified in the following manner. A wet and pale red colony was observed on YM agar (Becton Dickinson) plate medium, and the shape of the peripheral portion of the colony was relatively smooth. Microscopic features thereof were observed. As a result, formation of egg-shaped to oval and cylindrical trophocytes was observed, and trophocytes were found to proliferate due to gemmation. As a result of a biochemical property test, the results shown in Table 2 were obtained. Also, KSM-JL4651 grew at 30° C. but did not grow at 35° C. or higher.

TABLE 2

|  | KSM-JL2842 | KSM-J3571 | KSM-JL4651 |
|---|---|---|---|
| Carbon source assimilability test |  |  |  |
| D-Glucose | + | + | + |
| D-Galactose | + | + | + |
| L-Sorbose | + | + | w |
| D-Ribose | w | w | w |
| D-Xylose | + | + | + |
| L-Arabinose | + | + | + |
| D-Arabinose | + | w | w |
| L-Rhamnose | + | + | + |
| Sucrose | + | + | + |
| Maltose | + | + | + |

TABLE 2-continued

|  | KSM-JL2842 | KSM-J3571 | KSM-JL4651 |
|---|---|---|---|
| α,α-Trehalose | + | + | + |
| Me α-D-glucoside | + | + | w |
| D-Cellobiose | + | + | + |
| Salicin | − | w | w |
| Melibiose | + | + | + |
| Lactose | + | + | w |
| D-Raffinose | + | + | + |
| Melezitose | + | + | + |
| Inulin | − | w | − |
| Soluble starch | w | + | + |
| Glycerol | + | + | w |
| meso-Erythritol | + | + | w |
| Ribitol | w | − | w |
| D-Sorbitol | + | + | w |
| D-Mannitol | + | + | w |
| D-Galactitol | − | − | − |
| myo-Inositol | + | w | w |
| Glucono-1,5-lactone | w | w | − |
| Ca 2-keto-gluconic acid | − | − | w |
| Ca 5-keto-gluconic acid | − | − | w |
| DL-Lactate | + | + | w |
| Succinate | + | + | + |
| Citrate | − | w | w |
| Methanol | − | − | − |
| Sugar fermentability test | | | |
| D-Glucose | − | − | − |
| Nitrogen source assimilability test | | | |
| Potassium nitrate | + | + | + |

Subsequently, rDNAs of KSM-JL2842, KSM-J3571, and KSM-JL4651 were analyzed in the following manner. Specifically, the D1/D2 region of the 28S rDNA and the 18S rDNA were analyzed in accordance with the method of O'Donnell (O'Donnell, K. 1993, *Fusarium* and its near relatives, in Reynolds, D. R. and Taylor, J. W. (Eds) The Fungal Holomorph Mitotic, Meiotic and Pleomorphic Speciation in Fungal Systematics, CAB International, Wallingford) to deduce their taxonomic groups. The nucleotide sequences of the D1/D2 region of the 28S rRNA were determined, and the results are shown in SEQ ID NOs: 1 to 3. Also, the nucleotide sequences of 18S rDNA were determined, and the results are shown in SEQ ID NOs: 4 to 6. Identity search was conducted by BLAST.

The nucleotide sequence of the D1/D2 region of the 28S rDNA obtained from KSM-JL2842 exhibited 94.9% identity to the nucleotide sequence of *Pseudourotium zonatum* (AF096198), which is an *Ascomycetes* strain, and 94.6% identity to the nucleotide sequence of *Crinula caliciiformis* (AY544680). Also, the nucleotide sequence of 18S rDNA exhibited high identity; i.e., 98.8% identity to the nucleotide sequence of *Bulgaria inquinans* (AJ224362), which is an *Ascomycetes* strain, 98.9% identity to *ascomycete* sp. BBA71218 (AJ301960), and 98.9% identity to the nucleotide sequence of *Cryptosporiopsis radicicola* (DQ002903). However, it was difficult to deduce the taxonomic group of KSM-JL2842 into smaller classification than "class" level. Thus, it was concluded that the strain of interest was a yeast strain of a novel genus of *Ascomycetes*, which is classified in *Ascomycetes* class. The results of this example enabled identification of the strain of interest as *Ascomycete* sp. KSM-JL2842.

The nucleotide sequence of the D1/D2 region of the 28S rDNA obtained from KSM-J3571 exhibited 94.9% identity to the nucleotide sequence of *Pseudourotium zonatum* (AF096198), which is an *Ascomycetes* strain, 94.8% identity to the nucleotide sequence of *Leuconeurospora pulcherrima* (AF096193), and 94.6% identity to the nucleotide sequence of *Crinula caliciiformis* (AY544680). The nucleotide sequence of 18S rDNA exhibited 99.0% identity to the nucleotide sequence of *ascomycete* sp. BBA71218 (AJ301960), which is an *Ascomycetes* strain, and 98.8% identity to the nucleotide sequence of *Bulgaria inquinans* (AJ224362). However, it was difficult to deduce the taxonomic group of KSM-J3571 into smaller classification than "class" level. Thus, it was concluded that the strain of interest was a yeast strain of a novel genus of *Ascomycetes*, which is classified in *Ascomycetes* class. The results of this example enabled identification of the strain of interest as *Ascomycete* sp. KSM-J3571.

The nucleotide sequence of the D1/D2 region of the 28S rDNA obtained from KSM-JL4651 exhibited 94.6% identity to the nucleotide sequence of *Pseudourotium zonatum* (AF096198), which is an *Ascomycetes* strain, and 94.4% identity to the nucleotide sequence of *Leuconeurospora pulcherrima* (AF096193). The nucleotide sequence of 18S rDNA exhibited 99.0% identity to the nucleotide sequence of *ascomycete* sp. BBA71218 (AJ301960), which is an *Ascomycetes* strain, and 98.8% identity to the nucleotide sequence of *Bulgaria inquinans* (AJ224362). However, it was difficult to deduce the taxonomic group of KSM-JL4651 into smaller classification than "class" level. Thus, it was concluded that the strain of interest was a yeast strain of a novel genus of *Ascomycetes*, which is classified in *Ascomycetes* class. The results of this example enabled identification of the strain of interest as *Ascomycete* sp. KSM-JL4651.

*Ascomycete* sp. KSM-JL2842 and KSM-J3571 were deposited as of Jan. 12, 2006, under the accession numbers FERM BP-10713 and FERM BP-10712 and *Ascomycete* sp. KSM-JL4651 was deposited as of Jul. 13, 2006, under the accession number FERM BP-10714 at the International Patent Organism Depositary of the National Institute of Advanced Industrial Science and Technology (IPOD: Tsukuba Central 6, 1-1-1 Higashi, Tsukuba, Ibaraki, 305-8566, Japan).

Example 3

Examination of Ability of Producing dodecahydro-3a,6,6,9a-tetramethylnaphtho[2,1-b]furan intermediate In this example, the ability of *Ascomycete* sp. KSM-JL2842 for producing a dodecahydro-3a,6,6,9a-tetramethylnaphtho[2,1-b]furan intermediate was examined. At the outset, a platinum loopful of *Ascomycete* sp. KSM-JL2842 was inoculated into 2.1% YM broth (Becton Dickinson), shake-culture was conducted at 25° C. for 2 days, and the resultants were designated as starter strains. Subsequently, the starter strains were inoculated into a medium containing 2.1% YM broth, 0.1% magnesium sulfate heptahydrate, 1% Tween 80, and 2% sclareol to a concentration of 2%, and shake culture was conducted at 25° C. The culture solution was subjected to extraction and GC analysis via the method of Example 1, and the amounts of the dodecahydro-3a,6,6,9a-tetramethylnaphtho[2,1-b]furan intermediates to be produced were determined. The results are shown in Table 3. The units for the numerical values shown in Table 3 are "g/l."

TABLE 3

|  | 4 days | 7 days | 10 days |
|---|---|---|---|
| Sclareolide | 0.3 | 0.4 | 0.2 |
| Decahydro-2-hydroxy-2,5,5,8a-tetramethylnaphthaleneethanol | 12.0 | 15.7 | 14.5 |
| Cyclic ether | 0.5 | 0.4 | 0.8 |

The results shown in Table 3 demonstrate that *Ascomycete* sp. KSM-JL2842 can mainly produce decahydro-2-hydroxy-2,5,5,8a-tetramethylnaphthaleneethanol, among dodecahydro-3a,6,6,9a-tetramethylnaphtho[2,1-b]furan intermediates.

Example 4

Examination of Ability of Producing dodecahydro-3a,6,6,9a-tetramethylnaphtho[2,1-b]furan Intermediate In this example, the abilities of *Ascomycete* sp. KSM-JL2842, KSM-J3571, and KSM-JL4651 for producing dodecahydro-3a,6,6,9a-tetramethylnaphtho[2,1-b]furan intermediates were examined. At the outset, a platinum loopful of these strains were inoculated into a medium containing 0.2% yeast extract (Becton Dickinson), 0.2% ammonium nitrate, 0.1% monopotassium phosphate, 0.05% magnesium sulfate heptahydrate, and 1.0% glucose, shake culture was conducted at 25° C. for 2 days, and the resultants were designated as starter strains. Subsequently, the starter strains were inoculated into a medium containing 0.2% yeast extract (Becton Dickinson), 0.2% ammonium nitrate, 0.1% monopotassium phosphate, 0.05% magnesium sulfate heptahydrate, 1.0% glucose, 0.5% Tween 80, and 1.0% sclareol to a concentration of 1%, and shake culture was conducted at 25° C. for 6 days. The culture solution was subjected to extraction and GC analysis via the method of Example 1, and the amounts of the dodecahydro-3a,6,6,9a-tetramethylnaphtho[2,1-b]furan intermediates to be produced were determined. The results are shown in Table 4. The units for the numerical values shown in Table 4 are "g/l."

TABLE 4

| | KSM-JL2842 | KSM-J3571 | KSM-JL4651 |
|---|---|---|---|
| Sclareolide | 0.4 | 3.1 | 0.4 |
| Decahydro-2-hydroxy-2,5,5,8a-tetramethyl-naphthaleneethanol | 2.0 | 0.2 | 0.7 |
| Cyclic ether | Trace | 0.1 | Trace |

The results shown in Table 4 demonstrate that *Ascomycete* sp. KSM-JL2842, KSM-J3571, and KSM-JL4651 produce dodecahydro-3a,6,6,9a-tetramethylnaphtho[2,1-b]furan intermediates.

All publications, patents, and patent applications cited herein are incorporated herein by reference in their entirety.

The invention claimed is:

1. An isolated microorganism belonging to *Ascomycetes* and having the ability of producing an intermediate during a step of synthesizing dodecahydro-3a,6,6,9a-tetramethylnaphtho[2,1-b]furan using sclareol as a substrate, wherein said microorganism has 28S rDNA comprising a nucleotide sequence having 95% or higher identity to the nucleotide sequence as shown in any one of SEQ ID NOs: 1 to 3 or 18S rDNA comprising a nucleotide sequence having 95% or higher identity to the nucleotide sequence as shown in any one of SEQ ID NOs: 4 to 6.

2. The microorganism according to claim 1, which has mycological properties selected from the group consisting of the properties of KSM-JL2842, the properties of KSM-J3571, and KSM-JL4651. As shown in Table 1 below:

TABLE 1

|  | KSM-JL2842 | KSM-J3571 | KSM-JL4651 |
| --- | --- | --- | --- |
| Carbon assimilability test |  |  |  |
| D-Glucose | + | + | + |
| D-Galactose | + | + | + |
| L-Sorbose | + | + | w |
| D-Ribose | w | w | w |
| D-Xylose | + | + | + |
| L-Arabinose | + | + | + |
| D-Arabinose | + | w | w |
| L-Rhamnose | + | + | + |
| Sucrose | + | + | + |
| Maltose | + | + | + |
| α,α-Trehalose | + | + | + |
| Me α-D-glucoside | + | + | w |
| D-Cellobiose | + | + | + |
| Salicin | − | w | w |
| Melibiose | + | + | + |
| Lactose | + | + | w |
| D-Raffinose | + | + | + |
| Melezitose | + | + | + |
| Inulin | − | w | − |
| Soluble starch | w | + | + |
| Glycerol | + | + | w |

TABLE 1-continued

|  | KSM-JL2842 | KSM-J3571 | KSM-JL4651 |
| --- | --- | --- | --- |
| meso-Erythritol | + | + | w |
| Ribitol | w | − | w |
| D-Sorbitol | + | + | w |
| D-Mannitol | + | + | w |
| D-Galactitol | − | − | − |
| myo-Inositol | + | w | w |
| Glucono-1,5-lactone | w | w | − |
| Ca 2-keto-gluconic acid | − | − | w |
| Ca 5-keto-gluconic acid | − | − | w |
| DL-Lactate | + | + | w |
| Succinate | + | + | + |
| Citrate | − | w | w |
| Methanol | − | − | − |
| Sugar fermentability test |  |  |  |
| D-Glucose | − | − | − |
| Nitrogen assimilability test |  |  |  |
| Potassium nitrate | + | + | +. |

3. The microorganism according to claim 1, which is an ascomycetous yeast strain identified by the accession number FERM BP-10713, FERM BP-10712, or FERM BP-10714.

4. The microorganism according to claim 1, which belongs to the same genus as the *ascomycetous* yeast strain identified by the accession number FERM BP-10713, FERM BP-10712, or FERM BP-10714.

5. The microorganism according to claim 1, which belongs to the same species as the *ascomycetous* yeast strain identified by the accession number FERM BP-10713, FERM BP-10712, or FERM BP-10714.

6. The microorganism according to claim 1, which has the ability of producing decahydro-2-hydroxy-2,5,5,8a-tetramethylnaphthaleneethanol and/or sclareolide (decahydro-3a,6,6,9a-tetramethylnaphtho[2,1-b]furan-2(1H)-one) as an intermediate.

* * * * *

SEQUENCE LISTING

<160> NUMBER OF SEQ ID NOS: 6

<210> SEQ ID NO 1
<211> LENGTH: 611
<212> TYPE: DNA
<213> ORGANISM: Unknown
<220> FEATURE:
<223> OTHER INFORMATION: Ascomycete sp. KSM-JL2842

<400> SEQUENCE: 1

```
gcatatcaat aagcggagga aaagaaacca acagggatta cctcagtaac ggcgagtgaa     60
gcggtaacag ctcaaatttg aaatctggcc tcacggtccg agttgtaatt tgtagaggat    120
gcttcgggcg tggtccggtc taagttcctt ggaacaggac gtcatagagg gtgagaatcc    180
cgtatgtgac cgggtgccgc tgtccatgtg aagctccttc gacgagtcga gttgtttggg    240
aatgcagctc aaaatgggtg gtaaatttca tctaaagcta aatattggcc agagaccgat    300
agcgcacaag tagagtgatc gaaagatgaa aagcactttg gaaagagagt taaacagtac    360
gtgaaattgt tgaaagggaa gcgcttgcaa ccagacttgc acgcggtcga tcatcctgcc    420
ttctggctgg tgcactcgat cgcgttcagg ccagcatcgg ttttggtggt tggataaagg    480
ctctgggaat gtagcttctc tcggggagtg ttatagccca gggtgcaatg cagcctaccg    540
ggaccgagga ccgcgcttcg gctaggatgc tggcgtaatg gttgtaagcg acccgtcttg    600
aaacacggac c                                                        611
```

<210> SEQ ID NO 2
<211> LENGTH: 611
<212> TYPE: DNA
<213> ORGANISM: Unknown
<220> FEATURE:
<223> OTHER INFORMATION: Ascomycete sp. KSM-J3571

<400> SEQUENCE: 2

```
gcatatcaat aagcggagga aaagaaacca acagggatta cctcagtaac ggcgagtgaa     60
```

-continued

| | |
|---|---|
| gcggtaacag ctcaaatttg aaatctggcc tcacggtccg agttgtaatt tgtagaggat | 120 |
| gcttcgggcg tggtccggtc taagttcctt ggaacaggac gtcatagagg gtgagaatcc | 180 |
| cgtatgtgac cgggtgccgc tgtccatgtg aagctccttc gacgagtcga gttgtttggg | 240 |
| aatgcagctc aaaatgggtg gtaaatttca tctaaagcta atatggcc agagaccgat | 300 |
| agcgcacaag tagagtgatc gaaagatgaa aagcactttg gaaagagagt taaacagtac | 360 |
| gtgaaattgt tgaaagggaa gcgcttgcaa ccagacttgc acgcggtcga tcatcctgcc | 420 |
| ttctggctgg tgcactcgat cgcgttcagg ccagcatcgg ttttggtggt tggataaagg | 480 |
| ctctggggaat gtagcttctc tcgggagtg ttatagccca gggtgcaatg cagcctaccg | 540 |
| ggaccgagga ccgcgcttcg gctaggatgc tggcgtaatg gttgtaagcg acccgtcttg | 600 |
| aaacacggac c | 611 |

<210> SEQ ID NO 3
<211> LENGTH: 611
<212> TYPE: DNA
<213> ORGANISM: Unknown
<220> FEATURE:
<223> OTHER INFORMATION: Ascomycete sp. KSM-JL4651

<400> SEQUENCE: 3

| | |
|---|---|
| gcatatcaat aagcggagga aaagaaacca acagggatta cctcagtaac ggcgagtgaa | 60 |
| gcggtaacag ctcaaatttg aaatctggcc tcacggtccg agttgtaatt tgtagaggat | 120 |
| gcttcgggcg tggtccggtc taagttcctt ggaacaggac gtcatagagg gtgagaatcc | 180 |
| cgtatgtgac cgggtgccgc tgtccatgtg aagctccttc gacgagtcga gttgtttggg | 240 |
| aatgcagctc aaaatgggtg gtaaatttca tctaaagcta atatggcc agagaccgat | 300 |
| agcgcacaag tagagtgatc gaaagatgaa aagcactttg gaaagagagt taaacagtac | 360 |
| gtgaaattgt tgaaagggaa gcgcttgcaa ccagacttgc acgcggtcga tcatcctgcc | 420 |
| ttctggctgg tgcactcgat cgcgttcagg ccagcatcgg ttttggtggc tggataaagg | 480 |
| ctctggggaat gtagcttctc tcgggagtg ttatagccca gggtgcaatg cagcctgccg | 540 |
| ggaccgagga ccgcgcttcg gctaggatgc tggcgtaatg gttgtaagcg acccgtcttg | 600 |
| aaacacggac c | 611 |

<210> SEQ ID NO 4
<211> LENGTH: 1732
<212> TYPE: DNA
<213> ORGANISM: Unknown
<220> FEATURE:
<223> OTHER INFORMATION: Ascomycete sp. KSM-JL2842

<400> SEQUENCE: 4

| | |
|---|---|
| gtagtcatat gcttgtctca aagattaagc catgcatgtc taagtataag caatatatac | 60 |
| cgtgaaactg cgaatggctc attatatcag ttatagttta tttgatagta ccttactact | 120 |
| tggataaccg tggtaattct agagctaata catgctaaaa acctcgactt cggaagggt | 180 |
| gtatttatta gataaaaaac caatgcccct cggggctcac tggtgattca tgataactta | 240 |
| acgaatcgca tggccttgtg ccggcgatgg ttcattcaaa tttctgccct atcaactttc | 300 |
| gatggtagga tagtggccta ccatggtttc aacgggtaac ggggaattag ggttctattc | 360 |
| cggagaggga gcctgagaaa cggctaccac atccaaggaa ggcagcaggc gcgcaaatta | 420 |
| cccaatcccg acacgggag gtagtgacaa taaatactga tacagggctc ttttgggtct | 480 |
| tgtaattgga atgagtacaa tttaaatccc ttaacgagga acaattggag ggcaagtctg | 540 |

```
gtgccagcag ccgcggtaat tccagctcca atagcgtata ttaaagttgt tgcagttaaa      600
aagctcgtag ttgaaccttg ggcctggctg gccggtccgc ctcaccgcgt gcactggtcc      660
ggccgggcct ttccttctgg ggagccgcat gcccttcact gggtgtgtcg gggaaccagg      720
acttttactt tgaaaaaatt agagtgttca aagcaggcct atgctcgaat acattagcat      780
ggaataatag aataggacgt gtggttctat tttgttggtt tctaggaccg ccgtaatgat      840
taatagggat agtcggggc atcagtattc aattgtcaga ggtgaaattc ttggattat       900 tgaagactaa ctactgcgaa agcatttgcc aaggatgttt tcattaatca gtgaacgaaa      960
gttaggggat cgaagacgat cagataccgt cgtagtctta accataaact atgccgacta     1020
gggatcgggc gatgttatct ttttgactcg ctcggcacct tacgagaaat caaagttttt     1080
gggttctggg gggagtatgg tcgcaaggct gaaacttaaa gaaattgacg aagggcacc      1140 accaggagtg gagcctgcgg cttaatttga ctcaacacgg ggaaactcac caggtccaga     1200
cacaataagg attgacagat tgagagctct ttccttgattt tgtgggtggt ggtgcatggc     1260
cgttcttagt tggtggagtg atttgtctgc ttaattgcga taacgaacga gaccttaacc     1320
tgctaaatag ccaggctagc tttggctggt cgccggcttc ttagagggac tatcggctca     1380
agccgatgga agtttgaggc aataacaggt ctgtgatgcc cttagatgtt ctgggccgca     1440
cgcgcgctac actgacagag ccaacgagtt catcaccttg gccgaaaggt ctgggtaatc     1500
ttgttaaact ctgtcgtgct ggggatagag cattgcaatt attgctcttc aacgaggaat     1560
tcctagtaag cgcaagtcat cagcttgcgc tgattacgtc cctgcccttt gtacacaccg     1620
cccgtcgcta ctaccgattg aatggctcag tgaggctttc ggactgggcc agggaggtcg     1680
gcaacgacca cccagggccg gaaagttgtt caaacttggt catttagagg aa              1732
```

<210> SEQ ID NO 5
<211> LENGTH: 1772
<212> TYPE: DNA
<213> ORGANISM: Unknown
<220> FEATURE:
<223> OTHER INFORMATION: Ascomycete sp. KSM-J3571

<400> SEQUENCE: 5

```
gtagtcatat gcttgtctca aagattaagc catgcatgtc taagtataag caatatatac       60
cgtgaaactg cgaatggctc attatatcag ttatagttta tttgatagta ccttactact      120
tggataaccg tggtaattct agagctaata catgctaaaa acctcgactt cggaaggggt      180
gtatttatta gataaaaaac caatgccctt cggggctcac tggtgattca tgataactta      240
acgaatcgca tggccttgtg ccggcgatgg ttcattcaaa tttctgccct atcaactttc      300
gatggtagga tagtggccta ccatggtttc aacgggtaac ggggaattag ggttctattc      360
cggagaggga gcctgagaaa cggctaccac atccaaggaa ggcagcaggc gcgcaaatta      420
cccaatcccg acacggggag gtagtgacaa taaatactga tacagggctc ttttgggtct      480
tgtaattgga atgagtacaa tttaaatccc ttaacgagga acaattggag ggcaagtctg      540
gtgccagcag ccgcggtaat tccagctcca atagcgtata ttaaagttgt tgcagttaaa      600
aagctcgtag ttgaaccttg ggcctggctg gccggtccgc ctcaccgcgt gcactggtcc      660
ggccgggcct ttccttctgg ggagccgcat gcccttcact gggtgtgtcg gggaaccagg      720
acttttactt tgaaaaaatt agagtgttca aagcaggcct atgctcgaat acattagcat      780
ggaataatag aataggacgt gtggttctat tttgttggtt tctaggaccg ccgtaatgat      840
taatagggat agtcggggc atcagtattc aattgtcaga ggtgaaattc ttggattat       900
```

```
tgaagactaa ctactgcgaa agcatttgcc aaggatgttt tcattaatca gtgaacgaaa      960 gttagggat cgaagacgat cagataccgt cgtagtctta accataaact atgccgacta     1020
gggatcgggc gatgttatct ttttgactcg ctcggcacct tacgagaaat caaagttttt     1080
gggttctggg gggagtatgg tcgcaaggct gaaacttaaa gaaattgacg gaagggcacc     1140
accaggagtg gagcctgcgg cttaatttga ctcaacacgg ggaaactcac caggtccaga     1200
cacaataagg attgacagat tgagagctct ttcttgattt tgtgggtggt ggtgcatggc     1260
cgttcttagt tggtggagtg atttgtctgc ttaattgcga taacgaacga gaccttaacc     1320
tgctaaatag ccaggctagc tttggctggt cgccggcttc ttagagggac tatcggctca     1380
agccgatgga agtttgaggc aataacaggt ctgtgatgcc cttagatgtt ctgggccgca     1440
cgcgcgctac actgacagag ccaacgagtt catcaccttg gccgaaaggt ctgggtaatc     1500
ttgttaaact ctgtcgtgct ggggatagag cattgcaatt attgctcttc aacgaggaat     1560
tcctagtaag cgcaagtcat cagcttgcgc tgattacgtc cctgcccttt gtacacaccg     1620
cccgtcgcta ctaccgattg aatggctcag tgaggctttc ggactggccc agggaggtcg     1680
gcaacgacca cccagggccg gaaagttgtt caaacttggt catttagagg aagtaaaagt     1740
cgtaacaagg tctccgtagg tgaacctgcg ga                                    1772

<210> SEQ ID NO 6
<211> LENGTH: 1770
<212> TYPE: DNA
<213> ORGANISM: Unknown
<220> FEATURE:
<223> OTHER INFORMATION: Ascomycete sp. KSM-JL4651

<400> SEQUENCE: 6
gtagtcatat gcttgtctca aagattaagc catgcatgtc taagtataag caatatatac       60
cgtgaaactg cgaatggctc attatatcag ttatagttta tttgatagta ccttactact      120
tggataaccg tggtaattct agagctaata catgctaaaa acctcgactt cggaaggggt      180
gtatttatta gataaaaaac caatgcccct cggggctcac tggtgattca tgataactta      240
acgaatcgca tggccttgtg ccggcgatgg ttcattcaaa tttctgccct atcaactttc      300
gatggtagga tagtggccta ccatggtttc aacgggtaac ggggaattag ggttctattc      360
cggagaggga gcctgagaaa cggctaccac atccaaggaa ggcagcaggc gcgcaaatta      420
cccaatcccg acacggggag gtagtgacaa taaatactga tacagggctc ttttgggtct      480
tgtaattgga atgagtacaa tttaaatccc ttaacgagga caattggag gcaagtctg      540 gtgccagcag ccgcggtaat tccagctcca atagcgtata ttaaagttgt tgcagttaaa      600
aagctcgtag ttgaaccttg gcctggctg gccggtccgc ctcaccgcgt gcactggtcc      660
ggccgggcct ttccttctgg ggagccgcat gcccttcact gggtgtgtcg gggaaccagg      720
acttttactt tgaaaaaatt agagtgttca aagcaggcct atgctcgaat acattagcat      780
ggaataatag aataggacgt gtggttctat tttgttggtt tctaggaccg ccgtaatgat      840
taatagggat agtcggggc atcagtattc aattgtcaga ggtgaaattc ttggatttat      900
tgaagactaa ctactgcgaa agcatttgcc aaggatgttt tcattaatca gtgaacgaaa      960 gttagggat cgaagacgat cagataccgt cgtagtctta accataaact atgccgacta     1020
gggatcgggc gatgttatct ttttgactcg ctcggcacct tacgagaaat caaagttttt     1080
gggttctggg gggagtatgg tcgcaaggct gaaacttaaa gaaattgacg gaagggcacc     1140
accaggagtg gagcctgcgg cttaatttga ctcaacacgg ggaaactcac caggtccaga     1200
```

```
cacaataagg attgacagat tgagagctct ttcttgattt tgtgggtggt ggtgcatggc    1260
cgttcttagt tggtggagtg atttgtctgc ttaattgcga taacgaacga gaccttaacc    1320
tgctaaatag ccaggctagc tttggctggt cgccggcttc ttagagggac tatcggctca    1380
agccgatgga agtttgaggc aataacaggt ctgtgatgcc cttagatgtt ctgggccgca    1440
cgcgcgctac actgacagag ccaacgagtt catcaccttg gccgaaaggt ctgggtaatc    1500
ttgttaaact ctgtcgtgct ggggatagag cattgcaatt attgctcttc aacgaggaat    1560
tcctagtaag cgcaagtcat cagcttgcgc tgattacgtc cctgcccttt gtacacaccg    1620
cccgtcgcta ctaccgattg aatggctcag tgaggctttc ggactggccc agggaggtcg    1680
gcaacgacca cccagggccg gaaagttgtt caaacttggt catttagagg aagtaaaagt    1740
cgtaacaagg tctccgtagg tgaacctgcg                                    1770
```